(12) United States Patent
Beylund et al.

(10) Patent No.: US 7,854,720 B2
(45) Date of Patent: Dec. 21, 2010

(54) NEEDLE-FREE INJECTION SYSTEM (75) Inventors: Ryan R. Beylund, Milwaukie, OR (US); Keith K. Daellenbach, Portland, OR (US)

(73) Assignee: Bioject, Inc., Tualatin, OR (US)

( * ) Notice: Subject to any disclaimer, the term of this patent is extended or adjusted under 35 U.S.C. 154(b) by 0 days.

(21) Appl. No.: 12/624,061

(22) Filed: Nov. 23, 2009

(65) Prior Publication Data
US 2010/0069831 A1    Mar. 18, 2010

Related U.S. Application Data (62) Division of application No. 10/857,591, filed on May 28, 2004, now Pat. No. 7,717,874.

(51) Int. Cl.
*A61M 5/30* (2006.01)
(52) U.S. Cl. ..................................... 604/70
(58) Field of Classification Search ............ 604/68–72, 604/140, 141, 143, 148, 232, 131
See application file for complete search history.

(56) References Cited
U.S. PATENT DOCUMENTS

| | | | |
|---|---|---|---|
| 2,545,017 A | 3/1951 | Billingsley | |
| 2,653,602 A | 9/1953 | Smoot | |
| 2,667,874 A | 2/1954 | Dickinson, Jr. | |
| 2,680,439 A | 6/1954 | Sutermeister | |
| 3,110,309 A | 11/1963 | Higgins | |
| 3,115,133 A | 12/1963 | Morando | |
| 3,202,151 A | 8/1965 | Kath | |
| 3,292,621 A | 12/1966 | Banker | |
| 3,507,276 A | 4/1970 | Burgess | |
| 3,561,443 A | 2/1971 | Banker | |
| 3,688,765 A | 9/1972 | Gasaway | |

(Continued)

FOREIGN PATENT DOCUMENTS

EP    0427457    5/1991

(Continued)

OTHER PUBLICATIONS

Japanese Patent Office, Preliminary Notice of Reasons for Refusal, Aug. 4, 2009, 7 pages.

(Continued)

*Primary Examiner*—Manuel A Mendez
(74) *Attorney, Agent, or Firm*—Schwabe, Williamson & Wyatt, P.C.

(57) ABSTRACT

A needle-free injection device in which a gas cartridge or other source of pressurized gas is used to advance a piston and forcibly expel injectable fluid out through an injection orifice. When a gas cartridge is used, the gas cartridge may be moveable from an initial position to an actuating position in which gas is released to drive the injection, and a recoil inhibitor may be employed to prevent the gas cartridge from moving back to the initial position. A gas cartridge seal may be disposed on the gas cartridge and moveable with the gas cartridge to seal the gas cartridge against an interior wall of a gas cartridge housing. The needle-free injection device may also be configured so that sealing is compromised upon full advancement of the piston, so as to de-pressurize the device after delivery of an injection.

10 Claims, 7 Drawing Sheets

U.S. PATENT DOCUMENTS

| | | | |
|---|---|---|---|
| 3,695,266 | A | 10/1972 | Lussier |
| 3,714,943 | A | 2/1973 | Yanof et al. |
| 3,729,031 | A | 4/1973 | Baldwin |
| 3,802,430 | A | 4/1974 | Schwebel et al. |
| 3,853,125 | A | 12/1974 | Clark et al. |
| 3,859,996 | A | 1/1975 | Mizzy et al. |
| 3,940,003 | A | 2/1976 | Larson |
| 3,941,128 | A | 3/1976 | Baldwin |
| 3,945,379 | A | 3/1976 | Pritz et al. |
| 4,059,107 | A | 11/1977 | Iriguchi et al. |
| 4,124,024 | A | 11/1978 | Schwebel et al. |
| 4,266,541 | A | 5/1981 | Landau |
| 4,479,801 | A | 10/1984 | Cohen |
| 4,592,745 | A | 6/1986 | Rex et al. |
| 4,596,556 | A | 6/1986 | Morrow et al. |
| 4,652,261 | A | 3/1987 | Mech et al. |
| 4,662,878 | A | 5/1987 | Lindmayer |
| 4,680,027 | A | 7/1987 | Parsons et al. |
| 4,713,061 | A | 12/1987 | Tarello et al. |
| 4,717,384 | A | 1/1988 | Waldeisen |
| 4,747,839 | A | 5/1988 | Tarello et al. |
| 4,790,824 | A | 12/1988 | Morrow et al. |
| 4,850,967 | A | 7/1989 | Cosmai |
| 4,886,495 | A | 12/1989 | Reynolds |
| 4,909,794 | A | 3/1990 | Haber et al. |
| 4,913,699 | A | 4/1990 | Parsons |
| 4,940,460 | A | 7/1990 | Casey, I. et al. |
| 4,941,880 | A | 7/1990 | Burns |
| 5,009,637 | A | 4/1991 | Newman et al. |
| 5,024,656 | A | 6/1991 | Gasaway et al. |
| 5,049,128 | A | 9/1991 | Duquette |
| 5,064,413 | A | 11/1991 | McKinnon et al. |
| 5,080,648 | A | 1/1992 | D'Antonio |
| 5,135,514 | A | 8/1992 | Kimber |
| 5,273,544 | A | 12/1993 | Van der Wal |
| 5,318,522 | A | 6/1994 | D'Antonio |
| 5,334,144 | A | 8/1994 | Alchas et al. |
| 5,364,386 | A | 11/1994 | Fukuoka et al. |
| 5,383,851 | A | 1/1995 | McKinnon et al. |
| 5,399,163 | A | 3/1995 | Peterson et al. |
| 5,453,096 | A | 9/1995 | Lataix |
| 5,462,535 | A | 10/1995 | Bonnichsen et al. |
| 5,472,022 | A | 12/1995 | Michel et al. |
| 5,499,972 | A | 3/1996 | Parsons |
| 5,503,627 | A | 4/1996 | McKinnon et al. |
| 5,569,190 | A | 10/1996 | D'Antonio |
| 5,573,513 | A | 11/1996 | Wozencroft |
| 5,599,302 | A | 2/1997 | Lilley et al. |
| 5,645,538 | A | 7/1997 | Richmond |
| 5,704,911 | A | 1/1998 | Parsons |
| 5,716,348 | A | 2/1998 | Marinacci et al. |
| 5,730,723 | A | 3/1998 | Castellano et al. |
| 5,769,138 | A | 6/1998 | Sadowski et al. |
| 5,865,795 | A | 2/1999 | Schiff et al. |
| 5,891,085 | A | 4/1999 | Lilley et al. |
| 5,911,703 | A | 6/1999 | Slate et al. |
| 5,921,967 | A | 7/1999 | Sadowski et al. |
| 5,938,637 | A | 8/1999 | Austin et al. |
| 5,993,412 | A | 11/1999 | Deily et al. |
| 6,053,890 | A | 4/2000 | Moreau Defarges et al. |
| 6,056,716 | A | 5/2000 | D'Antonio et al. |
| 6,063,053 | A | 5/2000 | Castellano et al. |
| 6,080,130 | A | 6/2000 | Castellano |
| 6,096,002 | A | 8/2000 | Landau |
| 6,132,395 | A | 10/2000 | Landau et al. |
| 6,156,008 | A | 12/2000 | Castellano |
| 6,168,587 | B1 | 1/2001 | Bellhouse et al. |
| 6,210,359 | B1 | 4/2001 | Patel et al. |
| 6,224,567 | B1 | 5/2001 | Roser |
| 6,251,099 | B1 | 6/2001 | Kollias et al. |
| 6,264,629 | B1 | 7/2001 | Landau |
| 6,383,168 | B1 | 5/2002 | Landau et al. |
| 6,387,074 | B1 | 5/2002 | Horppu et al. |
| 6,406,455 | B1 | 6/2002 | Willis et al. |
| 6,471,669 | B2 | 10/2002 | Landau |
| 6,475,181 | B1 | 11/2002 | Potter et al. |
| 6,623,449 | B2 | 9/2003 | Paskar |
| 6,673,034 | B2 * | 1/2004 | Castellano .................. 604/68 |
| 6,905,475 | B2 | 6/2005 | Hauschild et al. |
| 2001/0004681 | A1 | 6/2001 | Landau |
| 2001/0051789 | A1 | 12/2001 | Parsons |
| 2002/0099329 | A1 | 7/2002 | Castellano |
| 2002/0123717 | A1 | 9/2002 | Landau |
| 2004/0111054 | A1 | 6/2004 | Landau et al. |
| 2004/0210188 | A1 | 10/2004 | Glines et al. |

FOREIGN PATENT DOCUMENTS

| | | |
|---|---|---|
| WO | 9737705 | 10/1997 |
| WO | 0113975 | 3/2001 |
| WO | 0137906 | 5/2001 |
| WO | 03103752 | 12/2003 |

OTHER PUBLICATIONS

European Patent Office, Communication Pursuant to Article 94(3) EPC, Aug. 10, 2009, 6 pages.
International Search Report for Application No. PCT/US2007/020254.
Written Opinion of the International Searching Authority for Application No. PCT/US2007/020254.

* cited by examiner

NEEDLE-FREE INJECTION SYSTEM

CROSS-REFERENCE TO RELATED APPLICATIONS

This application is a divisional of U.S. patent application Ser. No. 10/857,591, filed May 28, 2004 and entitled "NEEDLE-FREE INJECTION SYSTEM", the disclosure of which is herein incorporated by reference.

BACKGROUND

Needle-free injection devices provide an alternative to standard fluid delivery devices, which typically use a needle adapted to penetrate the outer surface of an injection site. Typically, needle-free injection devices are designed to eject the fluid from a fluid chamber with sufficient pressure to allow the fluid to penetrate the target to the desired degree. For example, common applications for needle-free injection devices include delivering intradermal, subcutaneous and intramuscular injections into or through a recipient's skin. For each of these applications, the fluid must be ejected from the system with sufficient pressure to allow the fluid to penetrate the tough exterior dermal layers of the recipient's skin.

Needle-free injection devices often employ pressurized gas to generate the force required to deliver injections. Various seals must be employed in such a device, so that as pressurized gas is applied, the resulting energy is captured and used effectively to deliver the injection. Inadequate sealing can result in waste of pressurized gas and/or an undesirable loss of control over the pressure at which the injection is delivered. In addition to sealing, various other design considerations are involved in providing injections with desired pressure characteristics.

Gas-powered and other needle-free injection devices may in some cases be pre-filled and/or configured to be used only once before disposal. With these devices, it will normally be desirable to reduce or eliminate the ability of an end user to disassemble or otherwise tamper with the device, or to use it other than as intended. Also, it will often be desirable to minimize manufacturing costs, accommodate different desired dosages with minimal modifications to the device and/or fabrication processes, and reduce contamination and other safety risks during and after use of the device.

DETAILED DESCRIPTION

Figures 1, 4A:
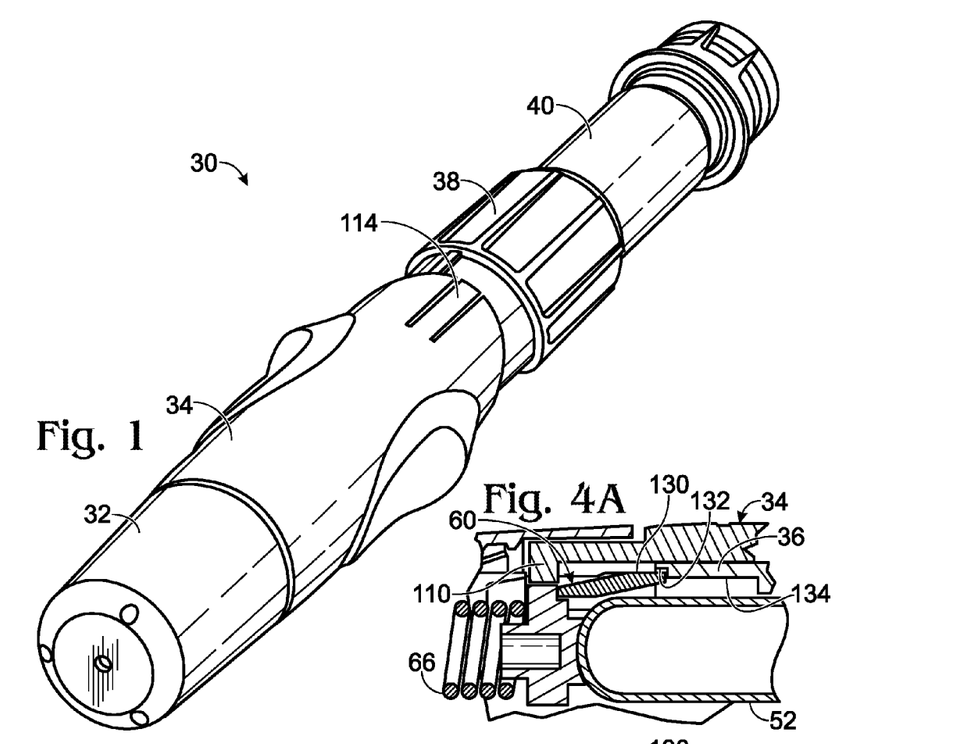
FIG. 1 is an isometric view of an embodiment of an injection device according to the present description.
FIGS. 4A, 4B and 4C are partial enlarged cross-sectional views of the injection device of FIG. 1, showing operation of an exemplary trigger mechanism that may be used to actuate delivery of an injection.
Figure 2:
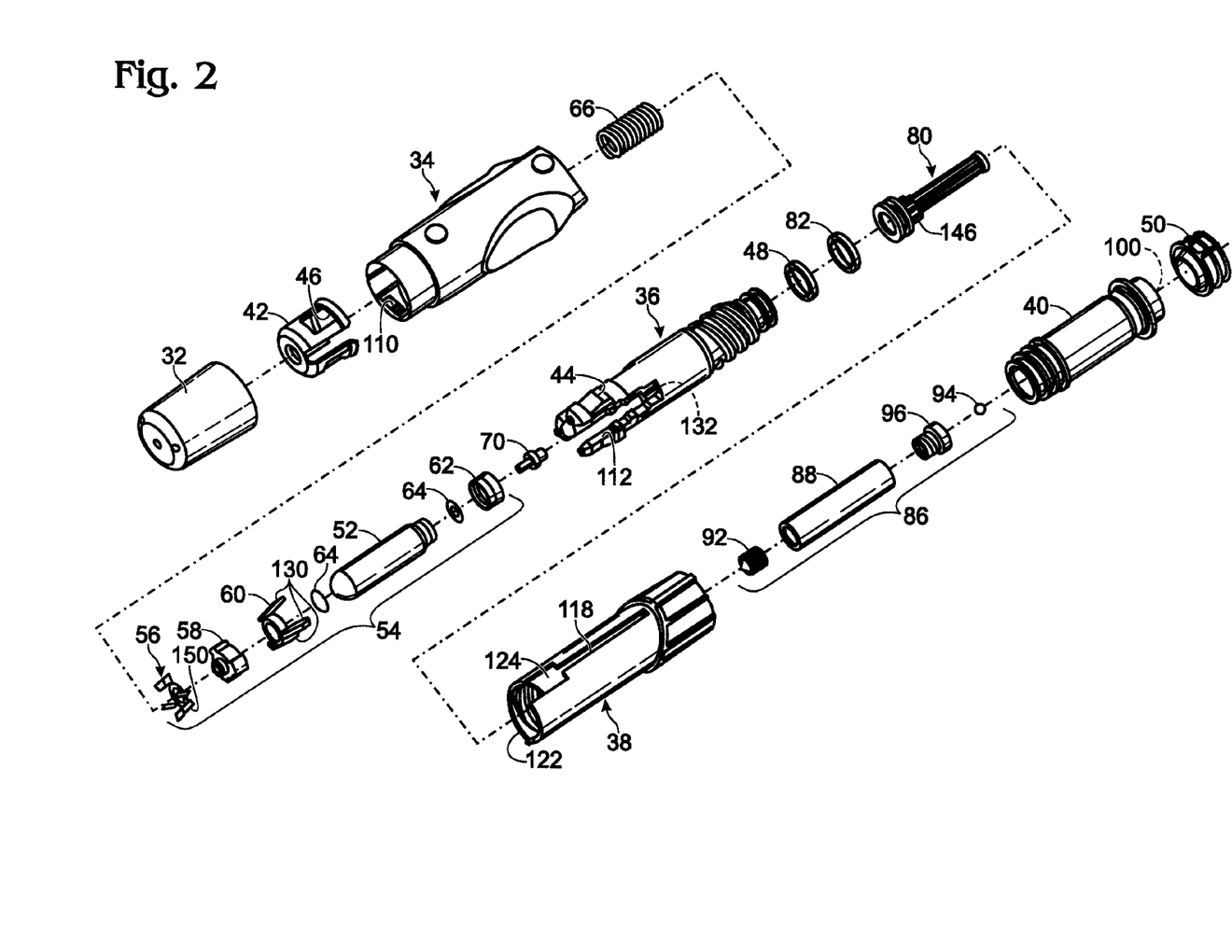
FIG. 2 is an exploded view of the injection device of FIG. 1.
Figure 3:
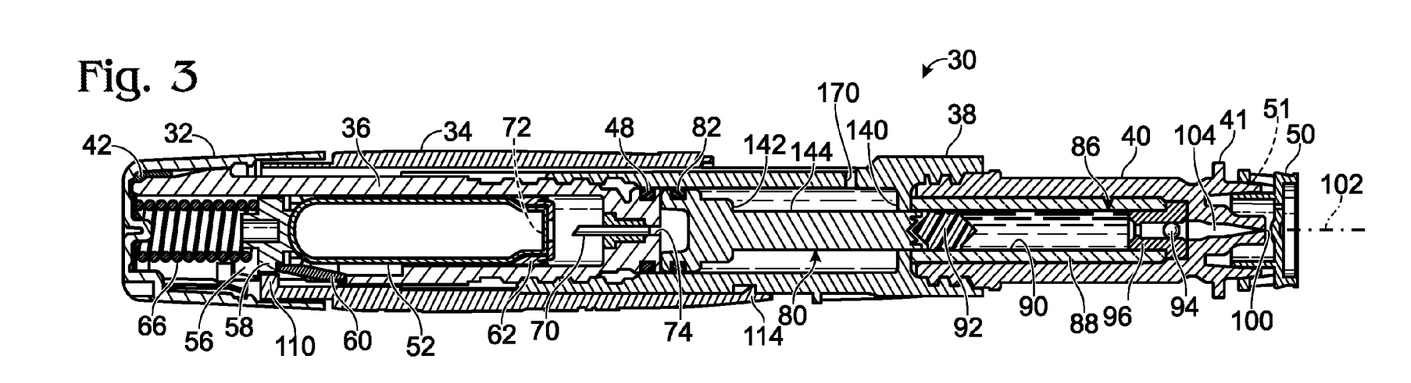
FIG. 3 is a cross-sectional view of the injection device of FIG. 1, showing the device in a storage position.

FIGS. 1-14 depict embodiments and alternate configurations of a needle-free injection device according to the present description. Referring first to FIGS. 1-3, various component parts of exemplary injection device 30 will be described, and with particular reference to FIG. 3, the device will be described as it is packaged, shipped and received by the end user.

Injection device 30 includes various outer structures within which other components are housed. These outer structures may include a back cover 32, trigger sleeve 34, back housing 36, front housing 38 and nozzle 40. Back cover 32 is fitted over a back cover clip 42, which may be secured to back housing 36 by snapping the back housing and back cover clip together. As shown in FIG. 2, the snap connection may be implemented so that protrusions 44 on back housing 36 are received within corresponding holes 46 formed on back cover clip 42.

Back housing 36 is threaded into front housing 38 so that a forward portion of the back housing is received within a rearward portion of the front housing. As explained below, a seal 48, such as an o-ring or u-cup seal, may be provided to provide a sliding sealing interface between the forward end of the back housing and the interior of the front housing. Typically, the threads on back housing 36 and front housing 38 are implemented as square threads (e.g., having a generally square or rectangular cross section), though triangular or other thread types may be employed.

Nozzle 40 may be provided at a forward end of device 30. In the depicted example, nozzle 40 is threaded into a forward end of front housing 38. As will be explained in more detail below, it may be desirable in some cases to provide a toothed surface or other thread-locking structure or mechanism to inhibit disassembly of nozzle 40 and front housing 38. A cap 50 may be provided at the forward end of nozzle 40 (i.e., the end through which the injection is delivered to the injection site) to guard against contamination prior to the device being used, such as during shipping and storage. As shown in FIG. 3, cap 50 may be configured to grip a circumferential rib 51 formed on the outer diameter of the forward end of nozzle 40. In addition, nozzle 40 may be provided with a large diameter flange 41 extending radially outward from the nozzle body. In certain manufacturing settings, flange 41 may facilitate handling of nozzle 40 by filling-line handlers and other machines used or during fabrication and preparation of the injection device.

Trigger sleeve 34 typically is positioned around back housing 36 and front housing 38. As explained in more detail below, trigger sleeve 34 is part of a trigger mechanism and may be used to rotate back housing 36 into front housing 38 to prime the injection device. Once the device is primed, the trigger sleeve may also be moved to actuate internal mechanisms, causing the injection to be delivered.

Typically, a power mechanism or other source of mechanical power is provided within the outer structures, to deliver the mechanical force (e.g., pressure) used to forcibly expel fluid from the injection device. For example, exemplary device 30 includes a pressurized gas source, such as gas cartridge 52, containing pressurized gas (e.g., nitrogen, carbon dioxide, etc.) which may be released to drive the injection. Gas cartridge 52 is part of a gas cartridge assembly 54 (FIG. 2) disposed within back housing 36, and which may further include a retaining spring 56, a hammer 58, a trigger 60 and a gas cartridge seal 62. Because the gas cartridge assembly is disposed within back housing 36, the back housing may also be referred to as the gas cartridge housing. Adhesive 64 may be provided to secure trigger 60 and gas cartridge seal 62 to gas cartridge 52, and/or to secure other components of the gas cartridge assembly together.

As will be explained in more detail below, a spring 66 may be positioned between gas cartridge assembly 54 and back cover clip 42, so as to urge the gas cartridge assembly forward. In the initial storage position shown in FIG. 3, trigger 60 engages a portion of back housing 36 so as to prevent spring 66 from decompressing and advancing the gas cartridge assembly forward. As will be explained below, trigger sleeve 34 and trigger 60 are part of a triggering mechanism, in which trigger sleeve 34 may be moved relative to back housing 36 so as to release the engagement of trigger 60 and back housing 36, thereby permitting gas cartridge assembly 54 to be advanced through decompression of spring 66.

A piercing member, such as pin 70, may be positioned within back housing 36. Pin 70 typically is of a hollow tubular construction, and is configured to pierce a pierceable sealed opening 72 on the forward end of gas cartridge 52. The hollow interior of pin 70 allows gas to be delivered through a hole 74 into an area or chamber partially bounded by front housing 38. Disposed within front housing 38 is a piston 80, and front housing 38 may thus alternately be referred to as the piston housing. The rearward end of piston 80 is positioned adjacent the forward end of back housing 36 near pin 70. The rearward end of the piston also typically is provided with a seal 82 (e.g., an o-ring or u-cup seal made of nitrile rubber or a like material) to sealingly engage the rearward end of the piston with the interior wall of front housing 38.

At the forward end of piston 80 is a drug cartridge assembly 86, including a drug cartridge 88 which defines a variable-volume injectable fluid chamber 90. Injectable fluid chamber 90 is sealed at one end with a plunger 92 and at the other end with a ball valve 94 and valve seal 96. Typically drug cartridge assembly 86 is housed within nozzle 40 or otherwise situated so that, upon opening of ball valve 94, injectable fluid chamber 90 is in fluid communication with an injection orifice 100 provided at the forward end of nozzle 40.

Typically, injection device 30 is pre-filled with a single dose of injectable fluid, and is disposed of after being used to deliver an injection. It will be appreciated, however, that the device may be modified to be filled by the end user and/or to be used multiple times. In addition, various features of the described exemplary device are applicable to a wide variety of other needle-free injection systems, including refillable systems, multiple use devices, and needle-free systems powered other than with compressed gas, such as spring-powered devices.

Various different materials may be employed with the injection device. In the describe exemplary device, back cover 32, trigger sleeve 34, hammer 58 back housing 36, piston 80, front housing 38 and nozzle 40 may be formed with polycarbonates, hard plastics or other like materials. Back cover clip 42, spring 66, retaining spring 56, piercing pin 70 and gas cartridge 52 are metal. Trigger 60 is made of a flexible plastic to enable legs 130 to be urged inward during actuation of the injection device. Seals 62, 48, 82, 96 and plunger 92 may be made of nitrile rubber or other materials providing desirable sealing properties. Drug cartridge 88 and valve 94 are made of glass. These materials may of course be varied as necessary and desirable, depending on the given injection application.

Figure 4:
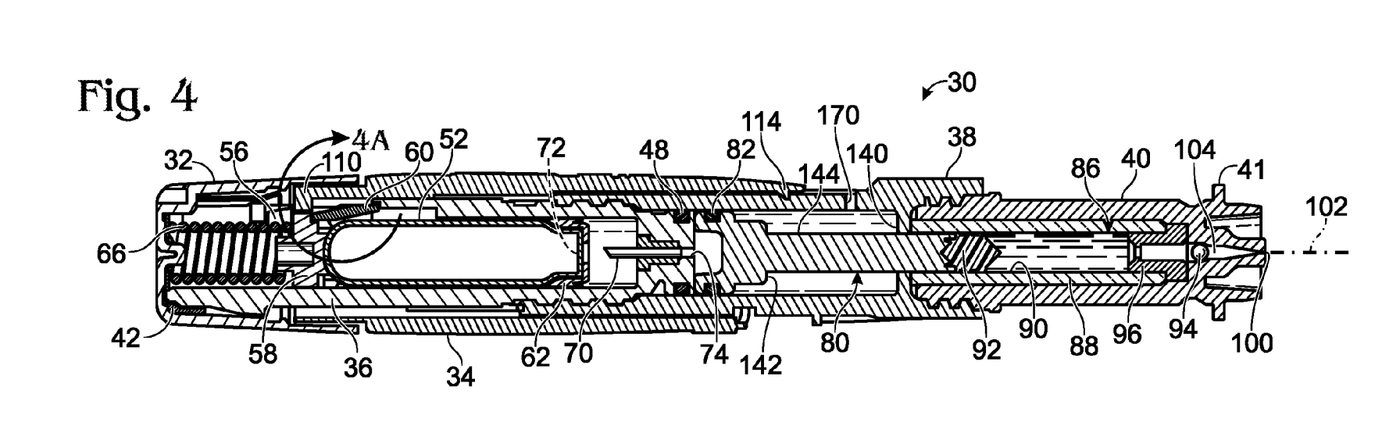
FIG. 4 is a cross-sectional view of the injection device of FIG. 1, showing the device in a primed position.
Figure 4B:
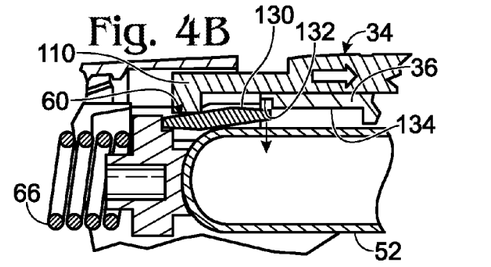
Figure 4C:
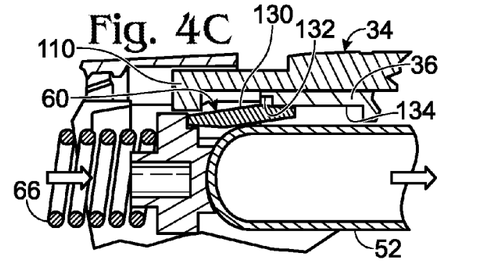
Figure 5:
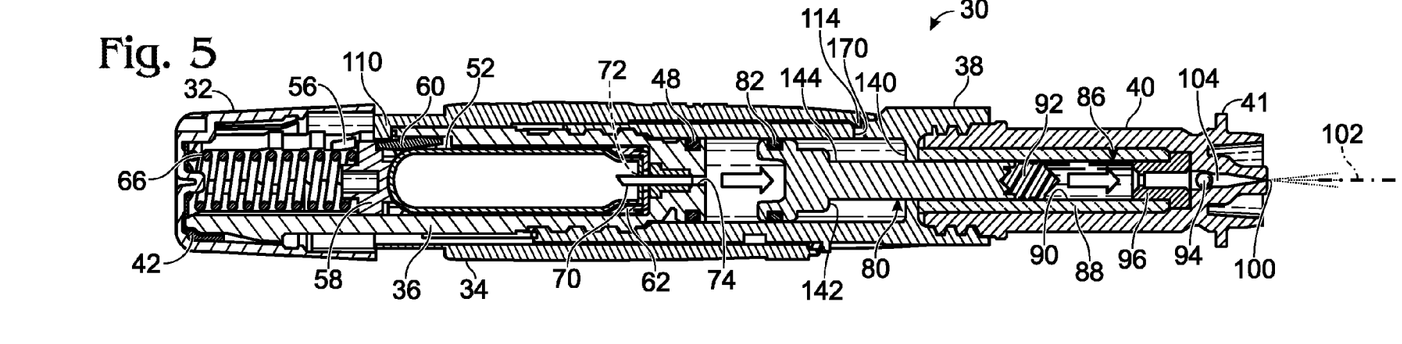
FIG. 5 is a cross-sectional view of the injection device of FIG. 1, showing the device during delivery of an injection.
Figure 6:
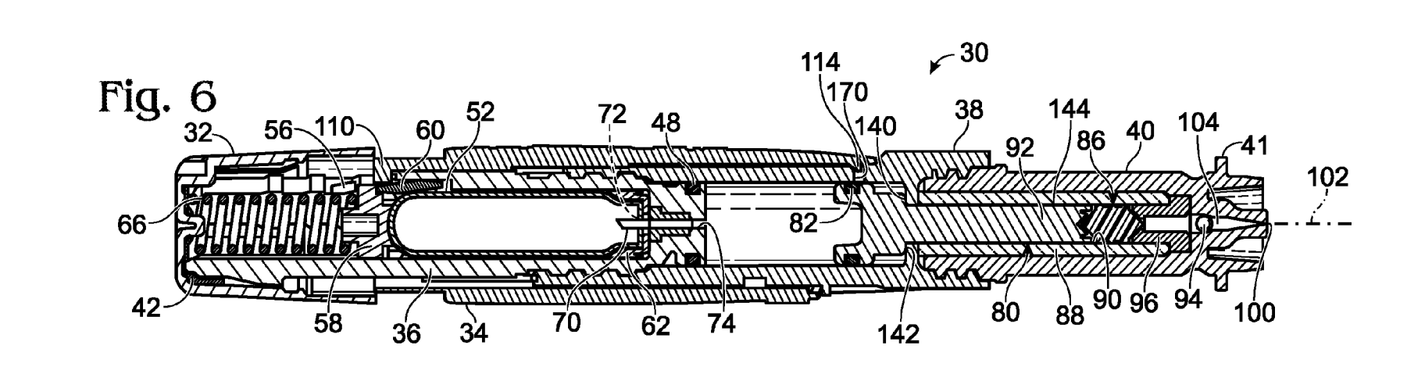
FIG. 6 is a cross-sectional view of the injection device of FIG. 1, showing the device in a dispensed position after delivery of an injection.

As indicated above, FIG. 3 shows device 30 in a ready state, corresponding to a configuration in which the device may be packaged, shipped and received by the end user. FIG. 4 shows the device after it has been primed; FIGS. 4A, 4B and 4C show interaction of trigger sleeve 34 with trigger 60 to release gas cartridge assembly 54 from its initial position, so that spring 66 can decompress and drive the gas cartridge forward onto piercing pin 70; FIG. 5 shows the device at an intermediate point during delivery of an injection while piston 80 is advancing to expel fluid from fluid chamber 90 out through injection orifice 100 along an injection axis 102; and FIG. 6 shows the device in a dispensed position after an injection has been delivered.

To use the device, cap 50 is first removed to expose injection orifice 100 at the forward end of nozzle 40. The device is then primed by causing piston 80 to slightly advance, which in turn advances plunger 92. The resulting hydrostatic force upon the injectable fluid within fluid chamber 90 causes ball valve 94 to pop out of engagement with valve seal 96, and into an area 104 forward of the valve seal between drug cartridge 88 and injection orifice 100. This allows injectable fluid to flow out of the drug cartridge and into the volume around ball valve 94. Accordingly, the injection device is primed with the entire volume upstream (e.g., rearward) of injection orifice 100 being filled with injectable fluid. This primed state is shown in FIG. 4.

In the depicted example, the initial advancement of piston 80 to prime the device is achieved by rotating back housing 36 relative to front housing 38. Because of the previously-described threaded connection between the housing pieces, this rotation causes back housing 36 to advance further into front housing 38 and push piston 80 slightly forward (e.g., from the storage position shown in FIG. 3 to the primed position shown in FIG. 4). Typically, trigger sleeve 34 and back housing 36 are engaged with each other so that the back housing may be rotated by rotating the trigger sleeve. Accordingly, in the depicted example embodiment, a user may prime the device by rotating trigger sleeve 34 relative to the rest of the device. It will be additionally noted from FIGS. 3 and 4 that several components to the rear of the device may rotate during priming. In particular, gas cartridge assembly 54 (FIG. 2), spring 66, back cover clip 42 and back cover 32 all rotate along with back housing 36 and trigger sleeve 34 during priming of the described exemplary device.

Referring now to FIGS. 2-8, the rearward end of trigger sleeve 34 includes three protrusions 110 spaced equally around the inner diameter of the trigger sleeve. The trigger sleeve is positioned relative to back housing 36 so that each protrusion 110 is situated within one of three corresponding elongate slots 112 formed on the rearward portion of back housing 36. Protrusions 110 extend radially inward from the inner diameter of the trigger sleeve and into slots 112. The radial inward extension of protrusions 110 is most clearly shown in FIG. 8. Protrusions 110 fit into slots 112 (FIG. 2) so that the trigger sleeve grips back housing 36 and the back housing rotates with the trigger sleeve about injection axis 102.

The forward end of trigger sleeve 34 includes a resilient tab 114 (FIGS. 1 and 3-7) that is pushed outward and bears against the outer surface of front housing 38 as trigger sleeve 34 is rotated during priming. Upon full rotation (e.g., approximately 180°) of the trigger sleeve from its initial position (FIG. 3) to the primed position (FIG. 4), tab 114 is received within an elongate groove 118 (FIG. 2) formed in the outer surface of front housing 38. Typically, trigger sleeve 34 and tab 114 are configured so that the tab makes a clicking sound as it falls into groove 118, thereby giving the user an audible indication that the device is primed and ready to be actuated to deliver the injection.

As will be explained in detail below, the depicted exemplary injection device is configured so that trigger sleeve 34 is slid forward relative to other components to trigger the injection. Typically, it will be desirable to prevent triggering until the injection device has been primed. In the depicted example, front housing 38 prevents trigger sleeve 34 from sliding forward until the trigger sleeve has been fully rotated to prime the device.

Figure 7:
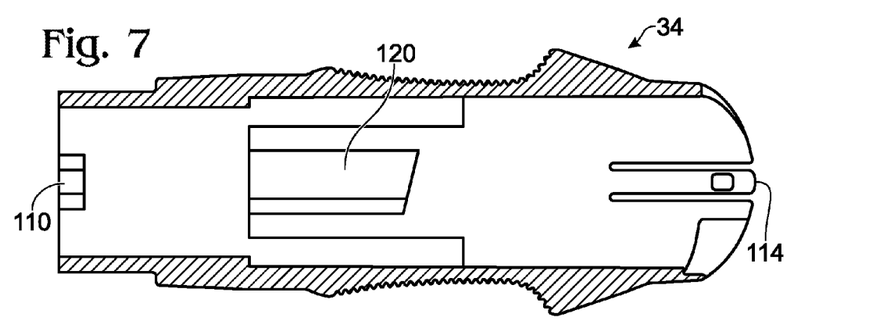
FIG. 7 is a cross-sectional view of an external housing structure that may be manipulated by the end user to prime the injection device of FIG. 1 and actuate delivery of an injection.
Figure 8:
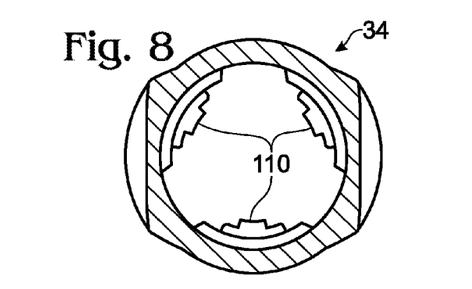
FIG. 8 is a cross-sectional end view of the external housing structure of FIG. 7.

Specifically, as shown in FIG. 7, a raised feature 120 is provided on the inner surface or diameter of trigger sleeve 34. Feature 120 extends far enough radially inward so that it abuts against rearward terminal edge 122 (FIG. 2) of front housing 38. As trigger sleeve 34 is rotated during priming, raised feature 120 rides on and against edge 122 until the fully primed position is achieved (FIG. 4), at which point the raised feature is aligned with a recess 124 (FIG. 2) provided on the rearward end of front housing 38. Recess 124 is adapted to accommodate and receive raised feature 120, such that upon priming of the device, trigger sleeve 34 can be advanced relative to the other components to actuate the injection.

In the depicted example, priming is achieved as describe above by threading the back housing into the front housing. In addition to or instead of this arrangement, priming may be achieved through other methods and/or different housing configurations may be employed. Back housing 36 and front housing 38 may, for example, be integrated as a single housing piece.

Referring back to FIG. 3, in the stored state of injection device 30, spring 66 is held in a compressed state by trigger 60. As shown in FIG. 2, trigger 60 may include three legs 130. In the stored state and primed state of FIGS. 3 and 4, gas cartridge assembly 54 is disposed relative to back housing 36 so that each of the three trigger legs is situated toward a forward end of one of the elongate slots 112 (FIG. 2) formed in back housing 36. In addition, as shown in FIG. 4A, the end of each trigger leg 130 abuts a ledge or lip 132 formed on the inside of back housing 36 adjacent the forward end of each elongate slot 112. The location of ledges 132 is also indicated in FIG. 2.

Trigger legs 130 are biased outward or otherwise positioned radially outward from injection axis 102 so that the trigger legs are positioned on ledges 132. In order to release the spring and actuate the injection, the trigger legs are moved radially inward. Then as spring 66 decompresses and drives gas cartridge 52 forward within back housing 36, the trigger legs are received within recesses 134 provided in back housing 36 just forward of ledges 132. The inward radial movement of the trigger legs and axial advancement of the trigger legs into recesses 134 are shown in FIGS. 4B and 4C.

The trigger legs are pushed radially inward to fire the device by sliding trigger sleeve 34 axially forward relative to back housing 36 and front housing 38. The change in axial position of trigger sleeve 34 may be seen by comparing FIG. 4 with FIG. 5 or 6. As previously described, protrusions 110 on the inside of the rearward end of trigger sleeve 34 are aligned with elongate slots 112 of back housing 36, and thus with legs 130 of trigger 60. Accordingly, as the trigger sleeve slides forward, protrusions 110 advance within elongate slots 112 and eventually come into contact with trigger legs 130, as shown in FIGS. 4A and 4B. As the trigger sleeve continues sliding forward, the protrusions eventually force the trigger legs radially inward so that the ends of the trigger sleeve fall off ledges 132, thereby permitting the gas cartridge assembly 54 to be advanced forward as a result of the force applied by spring 66 (FIG. 4C).

As spring 66 decompresses, gas cartridge is moved toward the actuating position so that pierceable sealed opening 72 is brought in to contact with pin 70. Compressed gas then escapes through the opening of the gas cartridge and through the hollow interior of pin 70 to act on a rearward end of piston 80. The pressurized gas drives piston 80 forward from its initial rearward-most position to its actuated forward-most position. As shown in FIG. 2 and FIGS. 3-6, the forward end of piston 80 may be formed with a conical-shaped cavity adapted to receive a corresponding conical surface of plunger 92. In any event, the advancement of piston 80 causes injectable fluid to be forcibly expelled from fluid chamber 90, around ball valve 94 and out through injection orifice 100. Typically, bypass channels are formed in nozzle 40 to permit fluid to flow around ball valve 94 to the injection orifice.

Various seals cooperate to seal the area behind piston 80 and thereby create a pressurized gas chamber upon release of gas from gas cartridge 52. Gas cartridge seal 62 seals between the forward end of the gas cartridge and the interior wall of back housing 36. Housing seal 48 seals back housing 36 to front housing 38, and piston seal 82 seals the rearward end of piston 80 against the interior wall of front housing 38. The seals thus cooperate to create a variable-volume sealed gas chamber to the rear of piston 80.

Referring particularly to gas cartridge seal 62, the seal typically is positioned on gas cartridge 52 so that the seal advances along with the gas cartridge as it is pushed within back housing 36 toward pin 70. As shown, seal 62 may be implemented with a V-shaped cross-section, and with the mouth of the "V" facing in a forward direction (e.g., with the mouth facing toward the pressurized area). Also, as in the depicted example, the gas cartridge seal typically will be positioned toward the forward end of the gas cartridge, around the narrowed neck area of the gas cartridge adjacent the pierceable opening. As a result, the volume that must be sealed is minimized, and is less than if the seal were formed at a fixed location in the gas cartridge housing wall and/or further rearward of the gas cartridge's tapered neck.

Referring to FIGS. 2 and 3-6, front housing 38 includes an obstruction 140 configured to stop advancement of piston 80 to control the piston stroke distance, i.e., the range of the piston's forward axial motion during delivery of an injection. Specifically, as indicated in the example, the obstruction may be implemented as a flange or constriction 140 that extends radially inward toward injection axis 102. Typically, the obstruction is adapted to interact with a stopper 142 provided on piston 80.

Stopper 142 may be implemented as a shoulder- or spacer-type structure that is spaced rearward of the forward operative end of the piston that drives plunger 92 forward. Stopper may be located in any desired position, though typically the stopper is closer to the rearward end of the piston than the forward end. Extending forward of stopper 142 is an elongate shaft portion 144, which is sized with a smaller cross section to extend through a hole formed in obstruction 140. Accordingly, as the piston advances, elongate shaft portion 144 is permitted to freely pass through the hole. In contrast, stopper 142 typically extends radially outward farther than elongate shaft portion 144, and thus cannot pass through the hole formed in obstruction 140. Accordingly, when stopper 142 housing obstruction 140 come into contact, further advancement of the piston is prevented, so as to define the forward-most end of the piston stroke.

As shown in FIG. 2, the piston stopper may be implemented as a plurality of axial ribs 146 extending forward from the sealed rearward end of piston 80. Additionally, or alternatively, a washer, spacer or other structure that is enlarged relative to shaft portion 144 may be used. Typically, stopper 142 and housing obstruction 140 are made of materials, such as a polycarbonate or other hard plastic, which are relatively hard and non-deformable compared to plunger 92. Also, piston 80 typically is sized so that piston stopper 142 bottoms out on housing obstruction 140 before plunger 92 (or other structure provided at the forward end of the piston) bottoms out on the forward end of fluid chamber 90. With these exemplary materials and configuration, piston 80 is stopped at its actuated position relatively abruptly, so as to produce a sharp and rapid reduction in injection pressure. Such a rapid decrease may be desirable in certain applications, to provide better control over the pressure profile of the injection and thereby eliminate or reduce wet injections, splashback and other potentially undesirable effects.

From the above, it will be appreciated that gas cartridge 52 moves from an initial position to an actuating position during initial actuation of the injection device. Specifically, the gas cartridge advances onto pin 70 so that pressurized gas is released to pressurize the gas chamber defined behind piston 80. This pressure acts upon piston 80, tending to drive it forward. The pressure also acts upon gas cartridge 52 and gas cartridge assembly 54, tending to drive those structures rearward. The rearward force upon the gas cartridge assembly can place significant strain upon various components of the injection device. Also, rearward movement of gas cartridge increases the pressurized volume behind piston 80, thereby producing variation in the injection pressure profile.

Accordingly, it may be desirable in some cases to prevent recoil of the gas cartridge. In particular, the described exemplary injection device may be provided with a recoil inhibitor or preventer configured to hold the gas cartridge in the advanced actuating position (e.g., the position at which the cartridge is pierced). Indeed, the recoil inhibitor typically is configured to constrain movement of the gas cartridge so that it is moveable from the initial position to the actuating position, but is prevented from moving from the actuating position back to the initial position.

Figure 9:
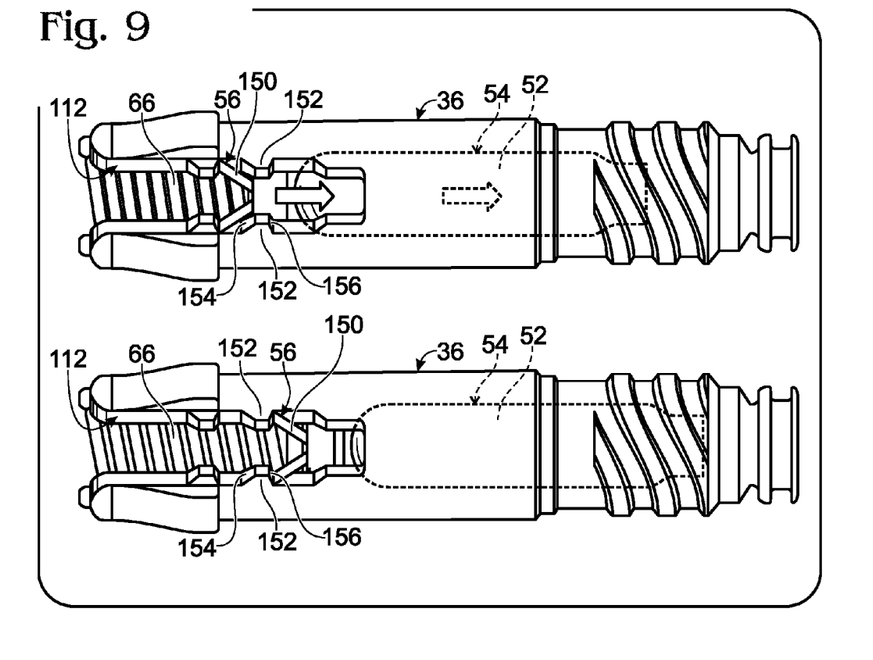
FIG. 9 depicts a recoil inhibiting mechanism that may be used in connection with the injection devices of the present description.

Recoil prevention is implemented in the exemplary embodiment through the interaction of retaining spring 56 and back housing 36. Referring to FIGS. 2 and 9, retaining spring 56 includes three pairs of legs 150. Each pair of legs is situated in one of the three elongate slots 112 provided on the rearward end of back housing 36. During storage and priming of the device, while gas cartridge assembly 54 is in its initial pre-actuated position relative to back housing 36 and front housing 38 (FIGS. 3 and 4), the retaining spring legs are situated in a rearward position (shown in the upper portion of FIG. 9).

During advancement of the gas cartridge assembly (i.e., movement occurring between position shown in upper and lower portions of FIG. 9), back housing slots 112 act as a ratchet, and retaining spring legs 150 act as a pawl, to permit unidirectional movement only of gas cartridge 52. Specifically, elongate slots 112 include protrusions or ratchet structures 152 that interact with legs 150 of retaining spring 56. As main spring 66 drives the gas cartridge assembly forward, each pair of angled retaining spring legs 150 is resiliently urged toward each other by ramped surfaces 154 of the ratchet structures (FIG. 9). As the gas cartridge assembly reaches the fully advanced actuating position, the retaining spring legs pop back outward as they pass over ratchet structures 152. This actuating position of the gas cartridge is shown in the lower portion of FIG. 9. In this advanced position, spring legs 150 abut against surfaces 156 of ratchet structures 152, which are vertical or at least less ramped than surfaces 154, such that gas cartridge 52 is prevented from moving rearward to its initial position. Accordingly, little or no strain is exerted upon back cover 32 or back cover clip 42 (FIG. 2), and the gas cartridge is firmly held within back housing 36 against the recoil which would otherwise result from the pressurized gas.

As previously discussed, pressurized gas is used in the described exemplary injection device to expel fluid from the injection device. Typically, upon completion of the injection the device will remain somewhat pressurized. For example, the gas chamber defined behind piston 80 typically will be at a pressure higher than atmospheric pressure after delivery of the injection, absent some further action to dissipate the elevated pressure. In some cases, it will be desirable to discharge this residual pressure, to safely dispose of the device or for other reasons.

Figure 10:
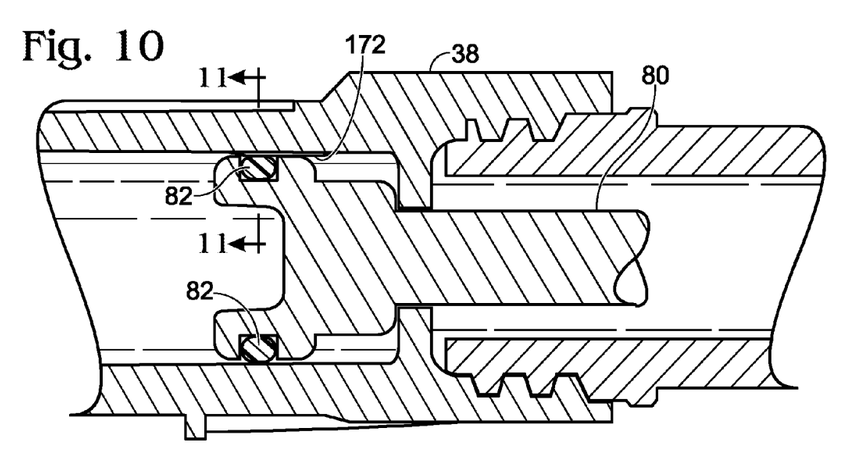
FIGS. 10 and 11 are enlarged partial cross-sectional views of the injection device of FIG. 1, depicting de-pressurization of the injection device.
Figure 11:
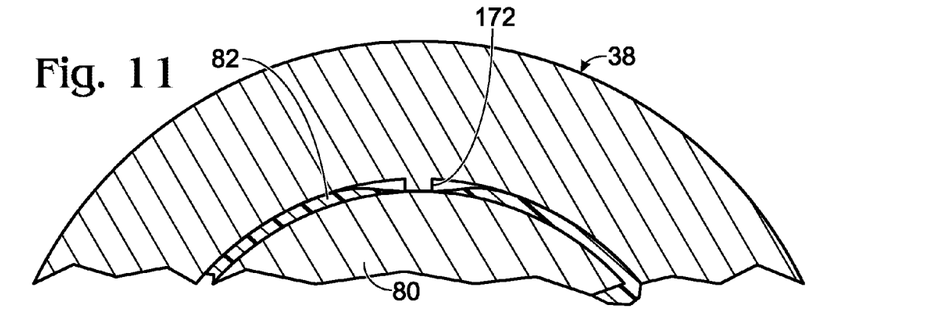

Accordingly, the injection device of the present description may be configured so that sealing is compromised at some point to ensure de-pressurization. Typically, the de-pressurization is implemented so that one or more of the pressurized gas chamber seals is compromised automatically (e.g., without user intervention or other added steps) upon full advancement of piston 80. As shown in FIGS. 3-6, front housing 38 may be provided with a hole 170 and, as shown in FIGS. 10 and 11, the interior wall of the front housing may be provided with a protrusion or other seal-compromising or seal-defeating irregularity, such as elongate rib 172.

Rib 172 is configured so that it impinges axially inward upon seal 82 when piston 80 is fully advanced. This impingement, which is shown particularly in FIG. 11, compromises the seal created by seal 82 between the piston and the interior wall of front housing 38. As a result, once the piston is fully advanced, gas is permitted to escape forward past seal 82 and out through hole 170 (FIGS. 3-6), allowing the area behind piston 80 to equalize with the surrounding atmospheric pressure. Typically, rib 172 extends rearward within front housing 38 so that compromising of seal 82 begins just prior to piston 80 reaching the end of its stroke. For example, the rib length may be such that impingement upon seal 82 does not occur until the piston has advanced at least 90% toward its forward-most position. It will be appreciated, however, that the device may be configured so that seal compromise occurs earlier in the piston stroke.

Figure 12:
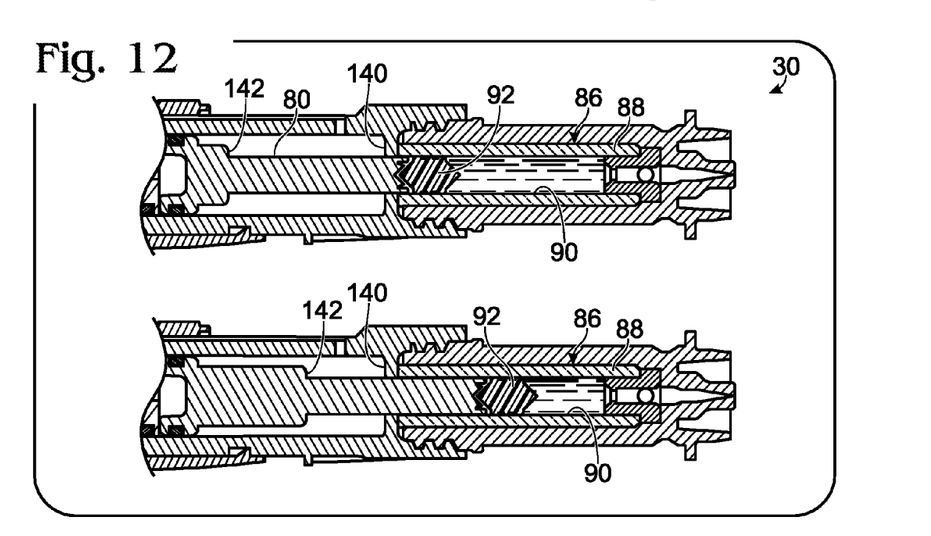
FIG. 12 depicts alternate embodiments of an injection device according to the present description, illustrating modification of a piston structure to adapt the injection device for use with different dosages.

Referring now to FIG. 12, injection device 30 may be modified to accommodate different dosage requirements. The upper portion of FIG. 12 shows a first embodiment configured for use with a dose of a given volume of injectable fluid. The lower portion of the figure shows an alternate embodiment configured to deliver an injection of approximately half the volume. To accomplish this, drug cartridge assembly 86 is initially prepared with the smaller volume of injectable fluid, such that the initial position of plunger 92 is farther forward within fluid chamber 90 (e.g., within drug cartridge 88).

It will therefore be appreciated that a correspondingly shorter piston stroke is desirable for the smaller-volume embodiment. To accomplish this, the overall length of piston 80 is increased, such that the forward end of the piston extends further into drug cartridge 88, consistent with the more advanced initial position of plunger 92. Also, the length of stopper portion 142 is increased so that the piston stroke is shorter and is abruptly terminated by interaction of stopper 142 with obstruction 140, as previously discussed. Indeed, the distance between stopper 142 and obstruction 140 typically is pre-selected based upon the desired piston stroke range and/or quantity of fluid to be expelled from fluid chamber 90. Using the above exemplary method, the device can accommodate different dosage requirements with minimal modifications to injection device 30, and/or to the processes used to manufacture the device.

In many applications, as previously discussed, it will be desirable to implement the injection device as a pre-filled unit that is shipped in a ready-to-use state and disposed after a single use. In such applications, it will often be desirable to reduce or eliminate the ability of the end user to disassemble or otherwise tamper with the device. For example, back cover clip 42 fits securely over back housing protrusions 44, making it difficult to disassemble the back end of the device. In addition, FIGS. 13 and 14 show an exemplary thread-locking arrangement that may be used toward the front end of device 30, to make it difficult to disassemble nozzle 40 from front housing 38.

Figure 13:
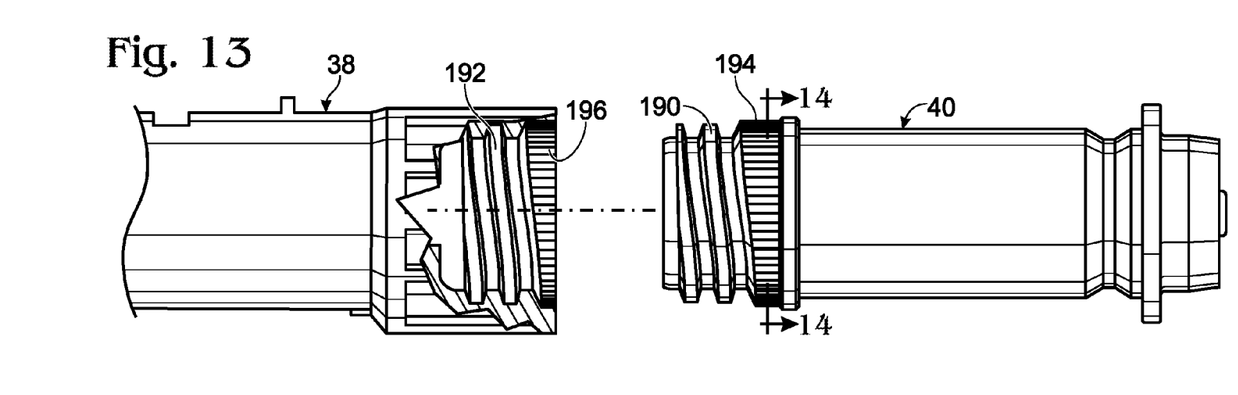
FIGS. 13 and 14 depict use of structures that may be employed with the present injection devices to inhibit disassembly of various housing components from each other.
Figure 14:
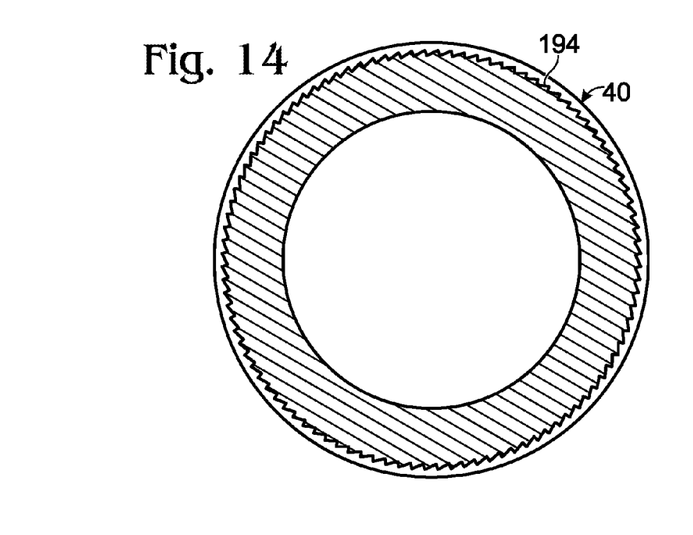

Referring first to FIG. 13, front housing 38 and nozzle 40 are shown exploded apart. The pieces are assembled by threading exterior threads 190 of nozzle 40 into interior threads 192 of front housing 38. A rearward portion of the nozzle is thus received partially within the forward end of front housing 38. As the nozzle is threaded into the front housing, the resulting relative axial motion eventually brings a toothed exterior surface 194 of the nozzle into engagement with a toothed interior surface of front housing 38. As shown in FIG. 13, for each of front housing 38 and nozzle 40, the toothed surfaces include teeth which are arranged so that they are generally perpendicular to the threads used to connect the pieces together.

During assembly, the nozzle and front housing are threaded into each other further after initial engagement of the toothed surfaces. Typically, the toothed surfaces are resilient and angled in an asymmetrical sawtooth configuration (the sawtooth configuration of the nozzle's toothed surface 194 is shown in FIG. 14). As a result of the toothed surfaces, and particularly because of the asymmetrical shape of the teeth, it is difficult to reverse the assembly process. The toothed surfaces substantially increase friction, and thus the torque required to rotate the pieces relative to one another, making it difficult or impossible for the end user to take the device apart.

While various embodiments and arrangements of a needle-free injection system and method have been shown and described above, it will be appreciated that numerous other embodiments, arrangements, and modifications are possible and are within the scope of the invention. The foregoing description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

What is claimed is:

1. A needle-free injection device, comprising,
    a housing;
    a piston disposed at least partially within the housing, the piston having a forward end and a rearward end, the piston being configured to advance relative to the housing from a rearward-most position to a forward-most position during delivery of an injection, so as to cause injectable fluid to be expelled out through an injection orifice;
    a pressurized gas source configured to deliver pressurized gas to act upon the rearward end of the piston;
    a seal at the rearward end of the piston, the seal being configured to seal a variable-volume gas chamber defined within the housing between the rearward end of the piston and the pressurized gas source; and
    an impingement on an interior surface of the variable-volume gas chamber, wherein the impingement is configured to compromise the piston seal upon advancement of the piston to the forward-most position, so as to de-pressurize the variable-volume gas chamber after delivery of an injection.

2. The device of claim 1, where the piston seal is compromised automatically without user intervention upon advancement of the piston to the forward-most position.

3. The device of claim 2, where the piston seal interacts with an interior wall of the housing to seal the variable-volume gas chamber, and where the obstruction comprises a seal-defeating irregularity formed on the interior wall in a location such that the seal comes into contact with the seal-defeating irregularity as the piston moves from the rearward-most position to the forward-most position.

4. The device of claim 3, where the seal-defeating irregularity is located on the interior wall of the housing so that the piston seal does not contact the seal-defeating irregularity until the piston has advanced substantially all the way to the forward-most position.

5. The device of claim 3, where the seal defeating irregularity includes an elongate rib formed on the interior wall of the housing.

6. The device of claim 3, where a vent hole is defined through the housing such that, upon contact of the piston seal with the seal-defeating irregularity, pressurized gas is permitted to escape from the variable-volume gas chamber past the gas seal and out through the vent hole.

7. The device of claim 1, where the pressurized gas source is a gas cartridge movably disposed within a gas cartridge housing so that the gas cartridge is movable from an initial position to an actuating position, in which a pierceable sealed opening at a forward end of the gas cartridge is pierced by a piercing member to enable pressurized gas to be released from the gas cartridge to act upon a rearward end of the piston, thereby driving the piston forward to forcibly expel injectable fluid out through an injection orifice.

8. The device of claim 7, further comprising a recoil inhibiter configured to constrain movement of the gas cartridge so that the gas cartridge is movable from the initial position to the actuating position, but is prevented from moving from the actuating position back to the initial position.

9. The device of claim 8, where the recoil inhibiter includes a ratchet structure and pawl device that interact to permit movement of the gas cartridge from the initial position to the actuating position and prevent movement of the gas cartridge from the actuating position back to the initial position.

10. The device of claim 7, further comprising a gas cartridge seal disposed on the gas cartridge and configured to move with the gas cartridge relative to the gas cartridge housing and sealingly engage an interior wall of the gas cartridge housing to inhibit gas from passing rearward past the gas cartridge seal between the gas cartridge and the gas cartridge housing.

* * * * *